US012295919B2

(12) United States Patent
Shibata et al.

(10) Patent No.: US 12,295,919 B2
(45) Date of Patent: May 13, 2025

(54) METHODS OF TREATMENT AND PREVENTION USING 4-DEOXY-L-ERYTHRO-5-HEXOSEULOSE URONIC ACID

(71) Applicant: MIE UNIVERSITY, Tsu (JP)

(72) Inventors: Toshiyuki Shibata, Tsu (JP); Hideo Miyake, Tsu (JP); Reiji Tanaka, Tsu (JP); Fumino Okuda, Tsu (JP); Mano Hasegawa, Tsu (JP)

(73) Assignee: MIE UNIVERSITY, Tsu (JP)

( * ) Notice: Subject to any disclaimer, the term of this patent is extended or adjusted under 35 U.S.C. 154(b) by 147 days.

(21) Appl. No.: 18/122,278

(22) Filed: Mar. 16, 2023

(65) Prior Publication Data

US 2023/0404938 A1    Dec. 21, 2023

(30) Foreign Application Priority Data

Mar. 16, 2022  (JP) ................................. 2022-041247

(51) Int. Cl.
| | | |
|---|---|---|
| A61K 31/7004 | (2006.01) | |
| A61K 31/047 | (2006.01) | |
| A61K 38/18 | (2006.01) | |
| A61P 25/28 | (2006.01) | |

(52) U.S. Cl.
CPC .......... *A61K 31/047* (2013.01); *A61K 38/185* (2013.01); *A61P 25/28* (2018.01)

(58) Field of Classification Search
CPC ...... A61K 31/047; A61K 38/185; A61P 25/28
See application file for complete search history.

(56) References Cited

U.S. PATENT DOCUMENTS

| | | |
|---|---|---|
| 9,506,090 B2 | 11/2016 | Kambourakis et al. |
| 10,927,363 B2 | 2/2021 | Shibata et al. |
| 2014/0017798 A1 | 1/2014 | Yu |
| 2014/0106414 A1 | 4/2014 | Kambourakis et al. |
| 2014/0206047 A1 | 7/2014 | Kambourakis et al. |
| 2014/0315318 A1 | 10/2014 | Lu et al. |
| 2015/0027206 A1 | 1/2015 | Lu |
| 2019/0127722 A1 | 5/2019 | Shibata et al. |

FOREIGN PATENT DOCUMENTS

| | | |
|---|---|---|
| JP | 2012210208 A | 11/2012 |
| JP | 2012235773 A | 12/2012 |
| JP | 6954644 B2 | 10/2021 |
| WO | 2013128285 A2 | 9/2013 |
| WO | 2014047510 A1 | 3/2014 |
| WO | 2015143381 A2 | 9/2015 |
| WO | 2015074025 A9 | 12/2015 |

OTHER PUBLICATIONS

Hu L-L, Chen C, Huang T, Cai Y-D, Chou K-C (2011) Predicting Biological Functions of Compounds Based on Chemical-Chemical Interactions. PLoS One 6(12): e29491. doi: 10.1371/journal.pone.0029491 (Year: 2011).*
Hu L-L, Chen C, Huang T, Cai Y-D, Chou K-C (2011) Predicting Biological Functions of Compounds Based on Chemical-Chemical Interactions. PLoS One 6(12): e29491 (Year: 2011).*
Chica, Robero A., et al., "Semi-rational approaches to engineering enzyme activity: combining the benefits of directed evolution and rational design", Curr Opin Biotechnol. 16(4):378-84 (2005).
Li, Shangyong, et al., "Cloning and characterization of the first polysaccharide lyase family 6 oligoalginate lyase from marine *Shewanella* sp. Kz7", J Biochem. Jan. 2016; 159(1):77-86, Epub (2015).
Mori, Tetsushi, et al. "Highly efficient alginate lyases from *Falsirhodobacter* sp. alg1"—Abstracts of Lectures of The Society for Biotechnology Japan, vol. 67, p. 97 (1P-036) Sep. 25, 2015.
Mori, Tetsushi, et al. "Screening for exolytic alginate lyases from marine bacteria"—Abstracts of Lectures of The Society for Biotechnology Japan, vol. 65, p. 59 (1P-166) Aug. 25, 2013.
Mori, Tetsushi, et al., "*Falsirhodobacter* sp. alg1 alyFRB gene for oligoalginate lyase, complete cds", May 26, 2016.
Mori, Tetsushi, et al., "*Falsirhodobacter* sp. alg1 alyFRA gene for endo-type alginate lyase, complete cds", May 26, 2016.
Mori, Tetsushi, et al., "*Falsirhodobacter* sp. alg1 gene for 16S ribosomal RNA, partial sequence", Mar. 13, 2014.
Mori, Tetsushi, et al., "*Falsirhodobacter* sp. alg1 Harbors Single Homologs of Endo and Exo-Type Alginate Lyases Efficient for Alginate Depolymerization", Plos One | DOI: 10.1371/journal.pone.0155537 May 13, 2016.
Mori, Tetsushi, et al., "Draft Genome Sequence of *Falsirhodobacter* sp. Strain alg1, an Alginate-Degrading Bacterium Isolated from Fermented Brown Algae", Genome Announc. Jul.-Aug. 2014; 2(4): e00826-14 (Year: 2014).
Nishi, S., et al., "alginate lyase precursor [Loktanella cinnabarina LL-001]", Database DDBJ/EMBL/GenBank [online], Accession No. GAD57170, Sep. 16, 2015 uploaded, [retrieved on May 12, 2017].
Nishi, S., et al., "oligo alginate lyase [Loktanella cinnabarina LL-001]", Database DDBJ/EMBL/GenBank [online], Accession No. GAD57174, Sep. 16, 2015 uploaded, [retrieved on May 12, 2017].

(Continued)

*Primary Examiner* — Kortney L. Klinkel
*Assistant Examiner* — Alison Azar Salamatian
(74) *Attorney, Agent, or Firm* — J-TEK LAW PLLC; Jeffrey D. Tekanic; Scott T. Wakeman

(57) ABSTRACT

A method of treating a patient in need thereof includes administering a therapeutically effective amount of 4-deoxy-L-erythro-5-hexoseulose uronic acid (DEH) to serve or function as a nerve growth factor (NGF) activity promoter, preferably to treat and/or prevent a neurodegenerative disease, such as PolyQ disease, Parkinson's disease, Parkinson's syndrome, spinocerebellar degeneration, spastic paraplegia, amyotrophic lateral sclerosis, Alzheimer's disease, dementia with Lewy bodies or corticobasal degeneration.

13 Claims, 9 Drawing Sheets

(56) References Cited

OTHER PUBLICATIONS

PET-22b(+) Vector, Novagen, created Dec. 10, 1998.
Sambrook, Joseph, et al., "Molecular Cloning a Laboratory Manual, 2nd edition", Cold Spring Harbor, N.Y. 1989, pp. 8.46-8.52 and pp. 11.2-11.19 (1989).
Singh, Ruashan Kumar, et al., "Protein Engineering Approaches in the Post-Genomic Era", Curr Protein Pept Sci. 2017, 18, 1-11 (2017).
Takahashi, Mami, et al, "Search for alginate lyases from brown-decomposing bacteria and evaluation of resolution"—Abstracts of the Marine Biotechnology Conference of Japanese Society for Marine Biotechnology, vol. 16, p. 53, May 31, 2015.
Takahashi, Mami, et al., "Characterization of alginate lyase AlyFRB obtained from brown algae *Falsirhodobacter* sp. alg1"—Abstracts of the Marine Biotechnology Conference of Japanese Society for Marine Biotechnology, vol. 17, p. 68 (0-1-5) May 30, 2015.
Wang, D.M., et al., "Optimal production of 4-deoxy-L-erythro-5-hexoseulose uronic acid from alginate for brown macro algae saccharification by combining endo- and exo-type alginate lyases", 2014, Bioprocess and Biosystems Engineering, vol. 37, p. 2105-2111.
Minakawa, E.N., et al., "Arginine is a disease modifier for polyQ disease models that stabilizes polyQ protein conformation", Brain 2020: pp. 1811-1825 (doi:10.1093/brain/awaa115).

\* cited by examiner 2 days 24 days

Detection of DEH from HBSS on the basement membrane
(AP to BL, 30 min.)

Control

Addition of NGF

Addition of NGF + addition of 50 μM DEH

METHODS OF TREATMENT AND PREVENTION USING 4-DEOXY-L-ERYTHRO-5-HEXOSEULOSE URONIC ACID

CROSS-REFERENCE

This application claims priority to Japanese patent application no. 2022-041247 filed on Mar. 16, 2022.

TECHNICAL FIELD

The present invention relates to a method of using 4-deoxy-L-erythro-5-hexoseulose uronic acid (DEH).

DEH is a rare sugar having unknown physiological function derived from alginic acid. The inventors have researched a method for producing DEH and published a part of it in Japanese Patent No. 6954644 and U.S. Pat. No. 10,927,363.

The present invention relates to the results of the following three commissioned research projects.
(1) 2022, the National Research and Development Agency, Japan Science and Technology Agency, research result deployment project University-originated new industry creation program "University/ecosystem promotion type start-up/ecosystem formation support" commissioned research,
(2) 2021, National Research and Development Agency, New Energy and Industrial Technology Development Organization, commissioned research,
(3) 2022, commissioned research by the New Energy and Industrial Technology Development Organization, National Research and Development Agency.

SUMMARY OF THE INVENTION

However, research on the physiological activity and applications of DEH has not progressed. Therefore, the inventors continued to study the physiological functions of DEH, and completed the present invention.

It is one non-limiting object of the present teachings to provide a new method for using DEH.

A composition for promoting nerve growth factor (NGF) activity according to one aspect of the present teachings is characterized by containing 4-deoxy-L-erythro-5-hexoseulose uronic acid (DEH).

A pharmaceutical composition according to another aspect of the present teachings contains 4-deoxy-L-erythro-5-hexoseulose uronic acid (DEH) as an active ingredient. Such a pharmaceutical composition may be used in a method for the treatment or prevention of one or more neurodegenerative diseases. The neurodegenerative disease(s) is (are) preferably at least one selected from the group consisting of polyglutamine (PolyQ) disease, Parkinson's disease, Parkinson's syndrome, spinocerebellar degeneration, spastic paraplegia, amyotrophic lateral sclerosis, Alzheimer's disease, dementia with Lewy bodies and corticobasal degeneration.

PolyQ disease is a general term for hereditary neurodegenerative diseases in which an abnormal extension (more than 40 times) of the CAG repeat sequence encoding glutamine forms PolyQ chains, which aggregate and cause neurodegeneration. It is estimated that there are about 10,000 patients in Japan, but no effective treatment has been found. PolyQ diseases include Huntington's disease, hereditary spinocerebellar ataxia (types 1, 2, 3, 6, 7, 17), dentatorubal-pallidoluysian atrophy, and spinobulbar muscular atrophy.

The inventors have found that DEH (1) is a rare sugar that can be absorbed from the intestinal tract, (2) can pass through the blood-brain barrier (BBB), and (3) assists the function of NGF and promotes synaptogenesis. Therefore, by administering a therapeutically effective amount of DEH to a patient in need thereof, it can be used for the prevention and/or treatment of dementia and the prevention and/or treatment of neurodegenerative diseases, because it is absorbed into the body, including the brain, and promotes synapse formation by NGF. Neurodegenerative diseases mean diseases which gradually lose specific neuronal cell groups (e.g., neuronal cells related to cognitive function, cells related to motor function) among the nerve cells in the brain and spinal cord. Specifically, polyglutamine disease, Parkinson's disease, Parkinson's syndrome (multiple system atrophy, progressive supranuclear palsy, etc.), spinocerebellar degeneration, spastic paraplegia, amyotrophic lateral sclerosis, Alzheimer's disease, dementia with Lewy bodies and corticobasal degeneration are examples thereof.

According to the present teachings, DEH can be provided for the prevention and/or treatment of neurodegenerative diseases.

BRIEF DESCRIPTION OF THE DRAWINGS

FIGS. 1A and 1B are micrographs of cultured Caco-2 cells, in which FIG. 1A shows a typical state after 2 days of culturing, and FIG. 1B shows a typical state after 24 days of culturing.

FIGS. 2A and 2B are schematic diagrams of model apparatuses for characterizing Caco-2 cell monolayers, in which FIG. 2A shows a model for measuring the TEER value of a single-layer membrane, and FIG. 2B shows a model for evaluating the permeability of a single-layer membrane using Lucifer yellow.

FIGS. 5A-5B are micrographs of PC-12 cells, in which FIG. 5A shows a Control, FIG. 5B shows NGF addition.

DETAILED DESCRIPTION OF THE INVENTION

Next, some embodiments of the present teachings will be described with reference to tables and the appended figures.

The technical scope of the invention is not limited by these embodiments, and can be implemented in various forms without changing the gist of the invention.

<Test 1> Confirmation of Membrane Permeability of DEH Using Caco-2 Cell Monolayer Membrane When Caco-2 cells (human colon cancer-derived cell line) are cultured in a monolayer on a porous membrane filter, they differentiate into intestinal epithelium-like cells. Owing to the differentiation, they express brush borders and tight junctions similar to columnar epithelial cells of the small intestine, as well as metabolic enzymes and transporters present in the human small intestine. Therefore, the Caco-2 cell monolayer is widely used as a model to predict absorption from the intestinal tract.

Using the Caco-2 cell monolayer, the membrane permeability of DEH was confirmed.

(1) Preparation of Caco-2 Cell Monolayer

Figure 1A:
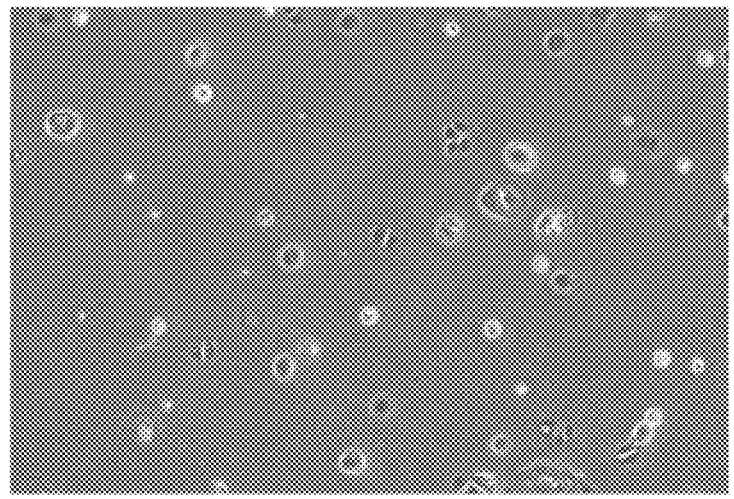
Figure 1B:

FIGS. 1A-1B show micrographs of Caco-2 cells on day 2 (FIG. 1A) and day 24 (FIG. 1B). On the 24th day, it was confirmed that brush borders and tight junctions were formed.

Figure 2A:
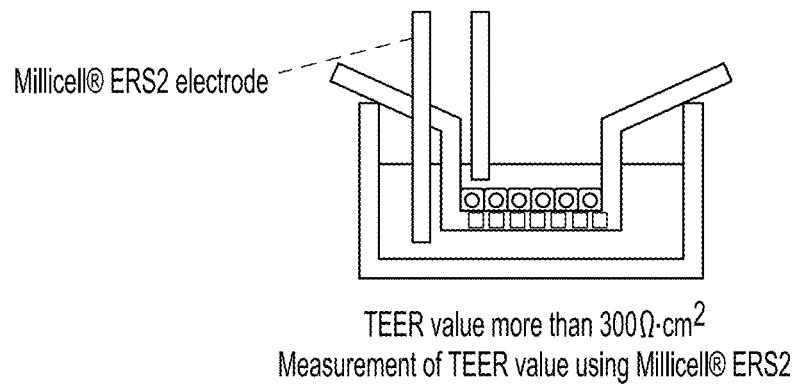
Figure 2B:
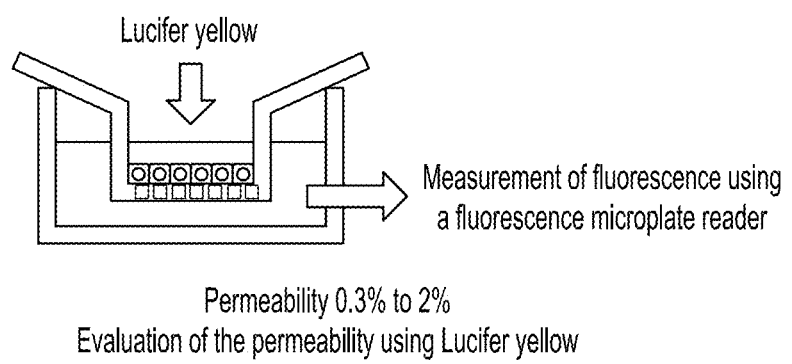

Next, using the model apparatuses shown in FIGS. 2A-2B, the electrical resistance value (transepithelial electrical resistance (TEER) value) using an electrical resistance system (voltohmmeter) sold under the trademark MILLI-CELL™ ESR-2 (FIG. 2A) and permeability using Lucifer Yellow (FIG. 2B) were measured to confirm that a single layer film was formed. The single layer films, in which the TEER value was more than 300 Ω·cm2 and the permeability of Lucifer yellow was 0.3% to 2%, were used in the test.

(2) Confirmation of Cytotoxicity by MTT Assay

Cytotoxicity tests were performed using MTT (3-(4,5-dimethylthiazol-2-yl)-2,5-diphenyltetrazolium bromide).

Figure 3:
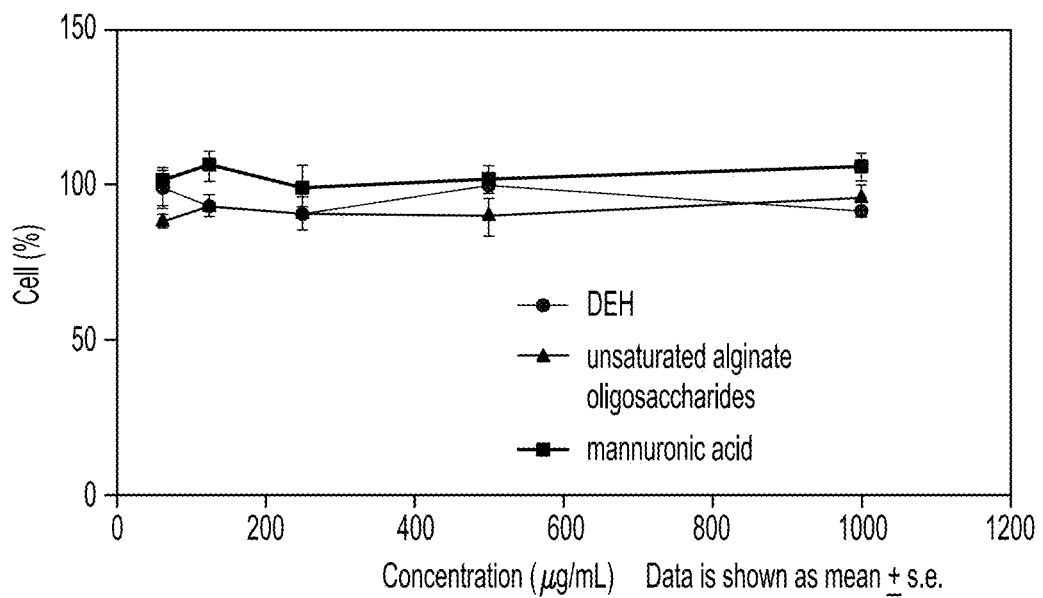
FIG. 3 is a line graph showing the results of a cytotoxicity test (MTT assay) using DEH, unsaturated alginate oligosaccharides and mannuronic acid.

FIG. 3 shows the results of cytotoxicity tests using DEH, unsaturated oligosaccharide alginic acid, and mannuronic acid. For all test substances, cell viability was almost 100% up to a concentration of 1000 μg/mL, and no cytotoxicity was confirmed.

(3) Confirmation of Membrane Permeability

Figure 4:
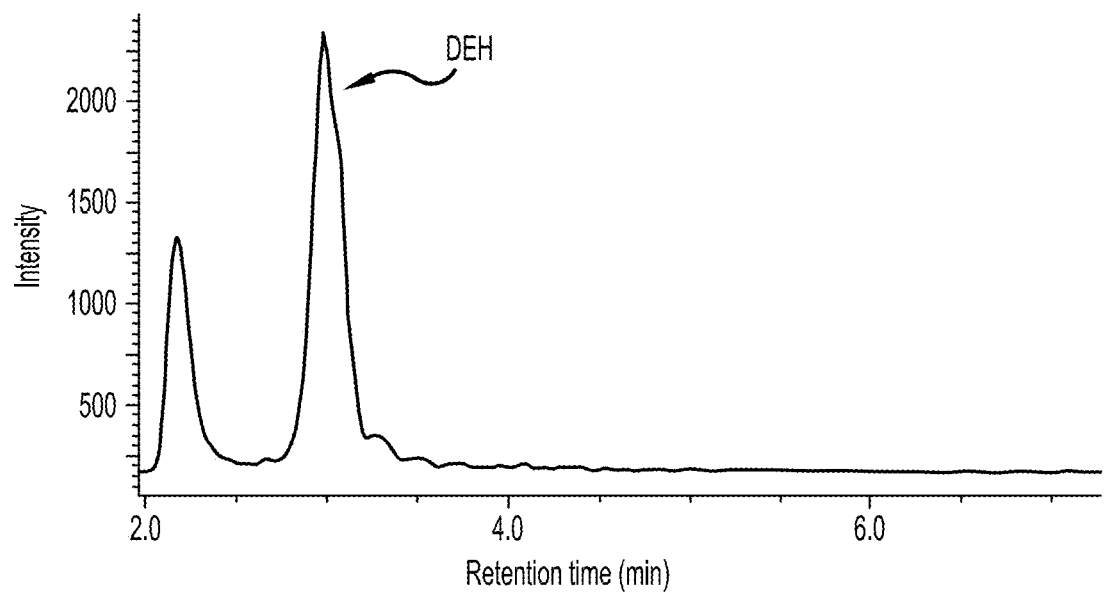
FIG. 4 is chromatogram showing the results of measuring DEH, which has permeated the membrane, by SIM measurement of LC/MS

FIG. 4 shows the results of DEH that had permeated from AP to BL at 30 minutes after the start of the test measured by a selective ion monitoring (SIM) measurement of liquid chromatography/mass spectrometry (LC/MS).

Permeability (absorption) of substances, which were added to the apical (AP: apical, luminal) side, to the basolateral (BL) side, or permeability (excretion) of substances, which were added to the BL side, to the AP side was evaluated.

Table 1 shows the apparent permeability (Papp) and Efflux ratio (ER) of DEH. An ER value of less than 2 means absorption from the intestinal tract, and an ER value of 2 or more means excretion from the intestinal tract. Table 2 shows the correlation between Papp and the absorption rate from the intestinal tract. These results indicate that DEH is a compound that corresponds to the moderate (20% to 70%) absorption category.

TABLE 1

Apparent permeability (Papp) and Efflux ratio (ER)

| $P_{app}$ (×10$^{-6}$ cm/s) | | ER |
|---|---|---|
| AP to BL | BL to AP | (B→A/A→B) |
| 5.13 ± 0.22 | 2.78 ± 0.12 | 0.542 |

Data is shown as mean ± s.e.

TABLE 2

Correlation between Papp and the absorption rate from the intestinal tract*

| Apparent permeability | Absorption category |
|---|---|
| $P_{app}$ < 1 × 10$^{-6}$ cm/s | Poor (0-20%) |
| $P_{app}$ = 1~10 × 10$^{-6}$ cm/s | Moderate (20-70%) |
| $P_{app}$ > 10 × 10$^{-6}$ cm/s | Good (70-100%) |

*Yee S. Pharmaceutical Research 14, 763-766 (1997)

<Test 2> Confirmation-1 of DEH Penetration into the Brain (Blood-Brain Barrier (BBB) Permeability) Using a Rat-Type Kit Next, DEH permeability was evaluated using a commercially available BBB kit (blood-brain barrier in vitro reconstitution system model (RBT-24H: PharmaCo-Cell Company Ltd.)). This kit uses endothelial cells, pericytes and astrocytes of Wistar rat origin. The above-mentioned SIM measurement of LC/MS was used in the detection and quantification of DEH. A 1000 μg/mL DEH solution was added to the blood vessel side, and after 30 minutes, culture medium on the brain parenchyma side was collected. Then, the DEH concentration in the collected culture medium was measured.

After the test, the DEH concentration in the brain parenchyma side was measured, and DEH permeability was calculated to be Papp=14.62±6.86×10$^{-6}$ cm/s. A summary of data, which examined permeability subgroups that migrate into the brain for various compounds, are shown in Table 3. According to Table 3, DEH was found to be a compound corresponding to the "good" permeability category.

TABLE 3

Permeability coefficient and intracerebral migration*

| $P_{app}$ (×10$^{-6}$ cm/s) | Permeability | Intracerebral migration |
|---|---|---|
| >20 | very good | easily transferred to the brain by passive diffusion, etc |
| 10~20 | good | transferred to the brain |
| 2~10 | low | transferred to the brain in a very small amount |
| 2< | very low | hardly transferred to the brain |

*Quoted from PharmaCo-cell HP www.pharmacocell.co.jp

<Test 3> Confirmation of Neurite Outgrowth Activity of DEH Using PC-12 Cells

Next, the characteristics of DEH were investigated using PC-12 cells. PC-12 cells are cells that were isolated from rat adrenal medullary pheochromocytoma and established as a strain. Nerve growth factor (NGF) is not needed for survival of PC-12 cells, but proliferation is arrested, nerve fibers elongate, and sympathetic ganglion neuron-like properties develop by using NGF. Owing to these properties, PC-12 cells have been used as a model for neural differentiation.

Figure 5A:
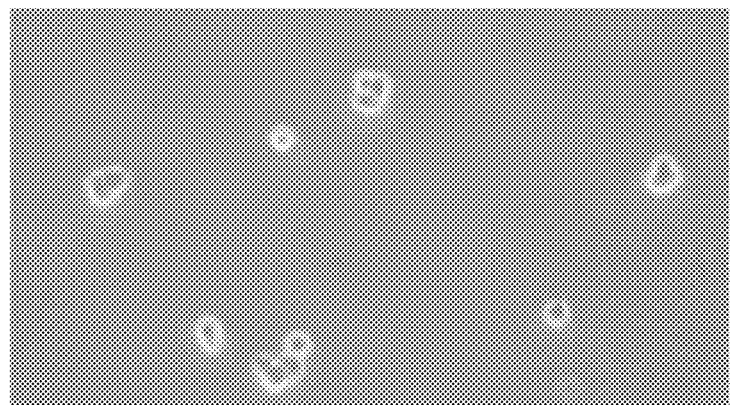
Figure 5B:
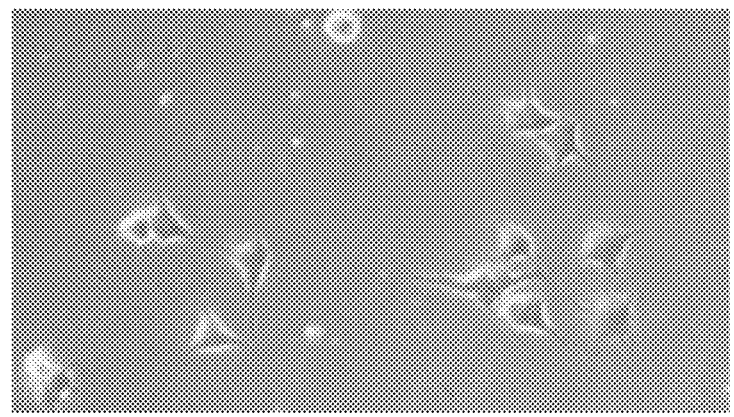
Figure 5C:
FIG. 5C shows NGF-addition+DEH addition (50 UM).
Figure 6:
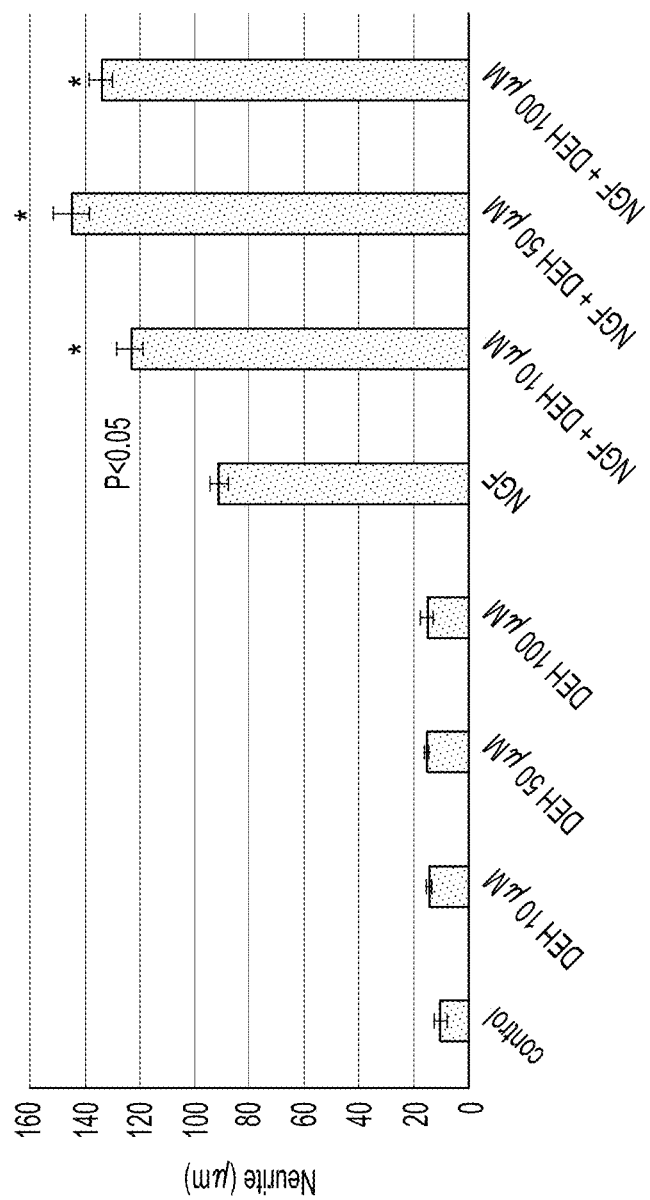
FIG. 6 is a bar graph showing the results of examining the length of neurites of each cell with no addition (Control), DEH addition (10, 50, 100 μM), NGF addition, NGF addition+DEH addition (10, 50, 100 μM). The symbol "*" in FIG. 6 indicates significance at a significance level of 5% ($p<0.05$) compared to NGF.

PC-12 cells were cultured and divided into 8 subgroups: no addition (Control), DEH addition (10, 50, 100 μM), NGF addition, NGF addition+DEH addition (10, 50, 100 μM), and elongation of neurite formation was observed. ImageJ software was used to measure neurite length. FIGS. 5A-5C show photographs of cells observed under a microscope; in FIG. 6 the neurite length (μm) of each subgroup is shown. Each data is shown as mean±standard error of triplicate tests. Statistical analysis was performed using the t-test, and a significance level of less than 5% (p<0.05) was considered significant. DEH alone did not induce neurite outgrowth, but DEH was found to significantly ($p<0.05$) promote the function of NGF in the NGF-added subgroup.

Figure 7:
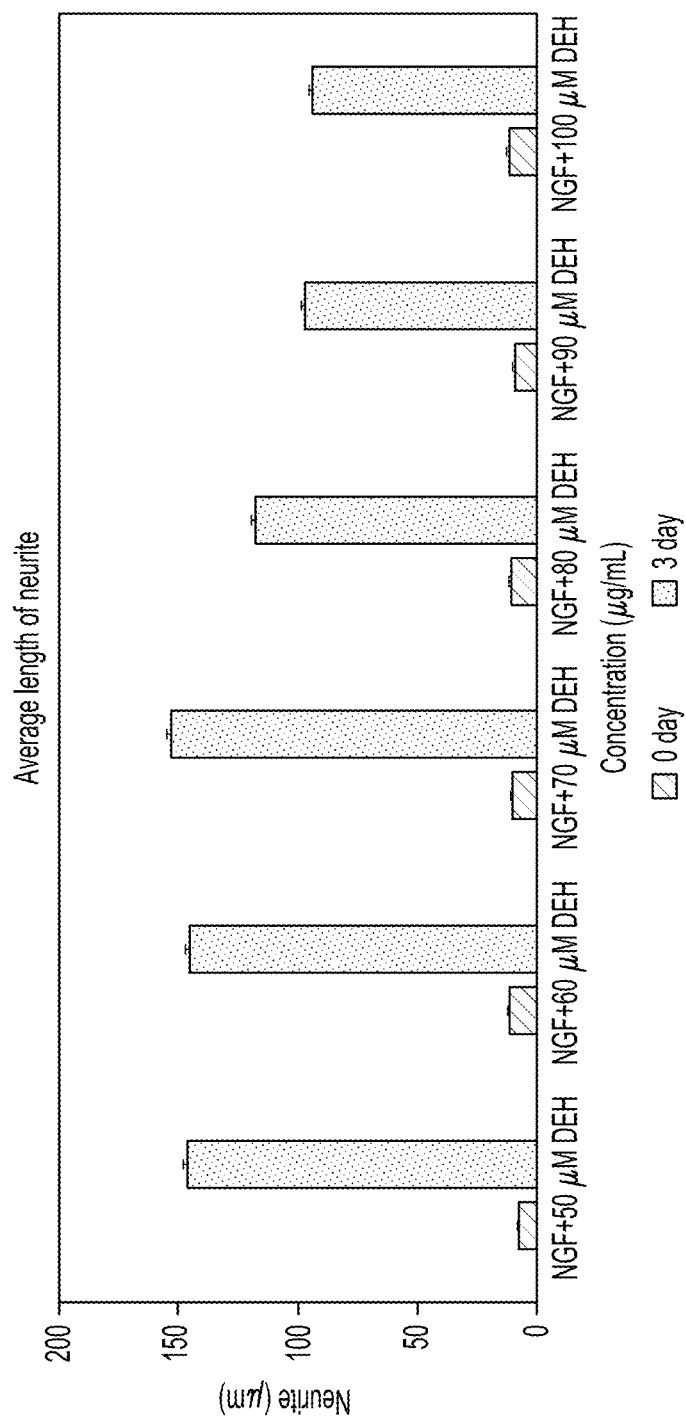
FIG. 7 is a bar graph showing the results of examining the length of neurites in each subgroup of NGF addition+DEH addition (50, 60, 70, 80, 90, 100 μM).
Figure 8:
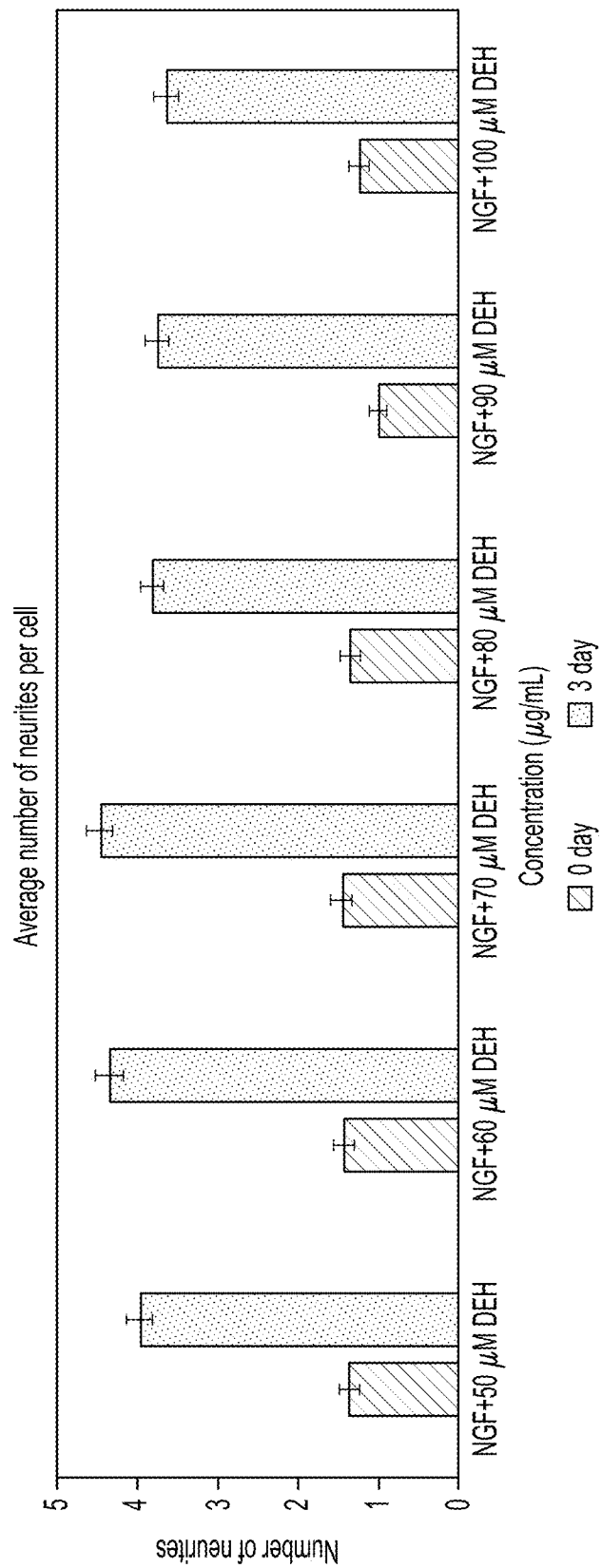
FIG. 8 is a bar graph showing the results in which the number of neurites in each subgroup of NGF addition+DEH addition (50, 60, 70, 80, 90, 100 μM) was examined.

NGF addition+DEH addition (50, 60, 70, 80, 90, 100 μM) was divided into 6 subgroups, and the elongation and number of neurites were observed and are shown in FIGS. 7 and 8. Each data is shown as mean±standard error of triplicate tests. It was found that the subgroup of 70 μM was the maximum for both neurite elongation and number, i.e. it was an optimum concentration.

<Test 4> Confirmation of DEH Membrane Permeability Using Human iPS Cell-Derived Intestinal Epithelial Cells The permeability of DEH through membrane was confirmed using human iPS cells. The intestinal epithelial cells induced from human iPS cells exhibit characteristics more similar to human small intestinal cells than the colon cancer-derived Caco-2 cells (large intestine-derived cells) used in <Test 1>. Therefore, results closer to the human body can be obtained using iPS cell-derived intestinal epithelial cells as compared to those using the Caco-2 cell model test.

(1) Preparation of Human iPS Cell-Derived Intestinal Epithelial Monolayer

Using a CO2 incubator (37° C., 5% CO2), human iPS cell-derived intestinal epithelial cells were cultured for 13 to 20 days to prepare a monolayer.

(2) Confirmation of Membrane Permeability

The membrane permeability of the human iPS cell-derived intestinal epithelial monolayer membrane was evaluated by the method described above in <Test 1> using an electrical resistance system (voltohmmeter) sold under the trademark MILLICELL™ ESR-2. Monolayer films, in which the TEER value was more 15002 cm2, were used in the test.

Permeability (absorption) of substances, which were added to the AP side, to the BL side, or permeability (excretion) of substances, which were added to the BL side, to the AP side was evaluated. The above-mentioned SIM measurement of LC/MS was used in the detection and quantification of DEH. Table 4 shows the apparent permeability (Papp) and Efflux ratio (ER) of DEH. With reference to the information shown above in Table 2, DEH was found to be a compound that falls into the moderate (20%-70%) absorption category.

TABLE 4

| Apparent permeability (Papp) and Efflux ratio (ER) | | |
|---|---|---|
| $P_{app}$ ($\times 10^{-6}$ cm/s) | | Efflux ratio (ER) |
| AP to BL | BL to AP | (B-A/A-B) |
| 8.78 ± 1.49 | 7.97 ± 1.26 | 0.907 |

Data is shown as mean ± s.e.

<Test 5> Confirmation-2 of DEH Penetration into the Brain (Blood-Brain Barrier (BBB) Permeability) Using a Cynomolgus Monkey-Type Kit The permeability of DEH was evaluated using a commercially available BBB kit (blood-brain barrier in vitro reconstitution system model (MBT-24H: PharmaCo-Cell Company, Ltd.)). The kit uses cynomolgus monkey-derived cells as endothelial cells. The permeability of DEH was evaluated using this model.

The reconstituted cynomolgus monkey BBB model has a structure closer to that of human BBB as compared to that of the kit in <Test 2>, so it was considered to be a better model for evaluating whether DEH permeates the human BBB.

After the test, the DEH concentration on the brain parenchyma side was obtained, and the DEH permeability was calculated. Table 5 shows the apparent permeability (Papp) and Efflux ratio (ER) of DEH.

TABLE 5

| Apparent permeability (Papp) and Efflux ratio (ER) | | |
|---|---|---|
| $P_{app}$ ($\times 10^{-6}$ cm/s) | | |
| Blood side (A) to Brain side (B) | Brain side (B) to Blood side (A) | Efflux ratio (ER) (B-A/A-B) |
| 2.88 ± 0.24 | 2.20 ± 0.55 | 0.766 |

Data is shown as mean ± s.e.

With reference to the information shown above in Table 3, DEH was found to be a compound corresponding to the "low" permeability category. Although the permeability of DEH was lower as compared to the results of <Test 2>, it was found that DEH is a compound that can penetrate the human BBB and migrate into the brain.

<Test 6> Confirmation of the Inhibitory Effect of DEH on Neuronal Death

The effect of DEH on neuronal death of the *C. elegans* strain HA759, which is a PolyQ disease model, was also investigated. HA759 strain (rtIs11 [osm-10p:: GFP+osm–10p: HtnQ150+dpy–20 (+)]) is a *C. elegans* strain which expresses Htn-Q150 (human huntingtin) and the fluorescent protein GFP downstream of the osm-10 gene when it receives a signal from ASH neurons. In accordance with the duration of the culture time, HA759 causes death of ASH neurons due to progressive neurodegeneration owing to accumulation of PolyQ.

Age-synchronized HA759 strain was cultured using mNGM medium. Control (DEH–), 25 mM DEH and 50 mM DEH were used as evaluation groups (samples). *E. coli* OP50-1 was used as nematode food.

Ten nematodes each were observed under a microscope immediately after the start of culture of the HA759 strain and after 24, 48, 72, and 120 hours to confirm whether nerve cells were alive or dead (n=30).

Figure 9:
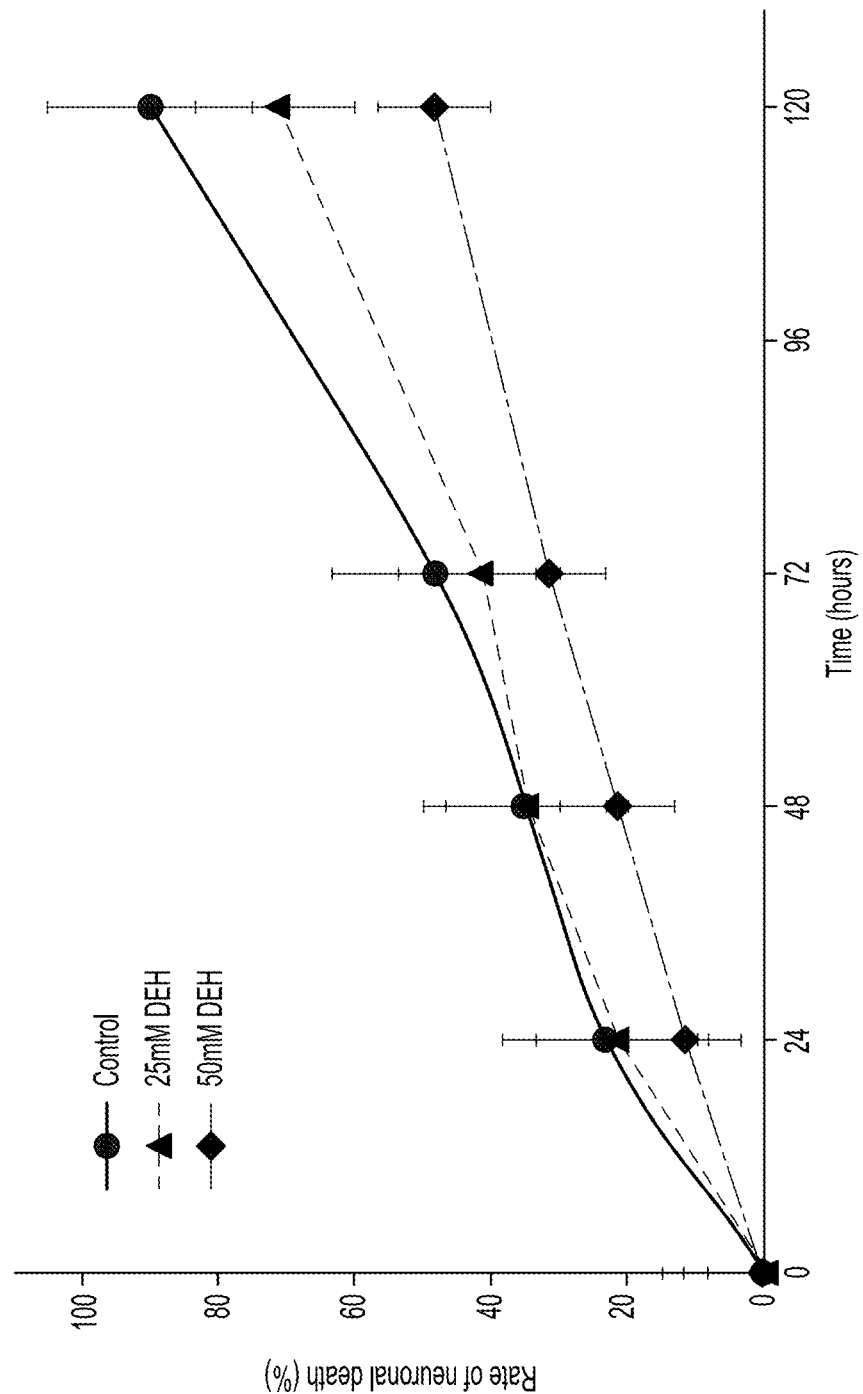
FIG. 9 is a graph showing the results in which the inhibitory effect of DEH on neuronal death was examined.

FIG. 9 shows the results of the examination of the rate of neuronal death in the *C. elegans* HA759 strain in medium containing each sample. Each data is shown as mean±standard error. At 120 hours after the start of culturing, neuronal death was suppressed (decreased) by 20.3% in the 25 mM DEH-treated group and by 46.4% in the 50 mM DEH-treated group as compared to the Control. Thus, DEH inhibited, in a dose-dependent manner, PolyQ-induced neuronal death in the HA759 strain. Because DEH suppresses (reduces) PolyQ aggregation and neuronal cell death, DEH can treat and/or prevent symptoms of PolyQ disease, such as involuntary movement and dementia.

<Test 7> Confirmation of the Effect of DEH on the Expression and Activation of DAF-16

The FOXO gene daf-16 is one of the components of the insulin/IGF-1 signaling pathway that controls many biological processes such as lifespan, metabolism, and stress response. When DAF-16 is localized in the nucleus, it activates the transcription of numerous genes involved in the regulation of stress tolerance promotion and pathogen protection. Therefore, the involvement of DEH in the activation of daf-16 was examined using the *C. elegans* TJ356 strain.

The TJ356 strain (zIs356 [daf-16p::daf-16a/b::GFP+rol-6 (su1006)]) is a nematode, in which a fluorescent protein GFP has been inserted into the daf-16 promoter, and nuclear translocation by daf-16 gene activation can be observed by fluorescence of the GFP.

Age-synchronized TJ356 strain was cultured using mNGM medium at 20° C. for 72 hours. As evaluation groups (samples), positive control (group heat-treated at 37° C. for 30 minutes after 72-hour culture), control (DEH−), 25 mM DEH and 50 mM DEH were used. *E. coli* OP50-1 was used as nematode food.

After culturing the TJ356 strain, 15 nematodes in each group were observed under a microscope to confirm the presence or absence of nuclear localization of the DAF-16 protein (GFP fluorescence) (n=60).

Figure 10:
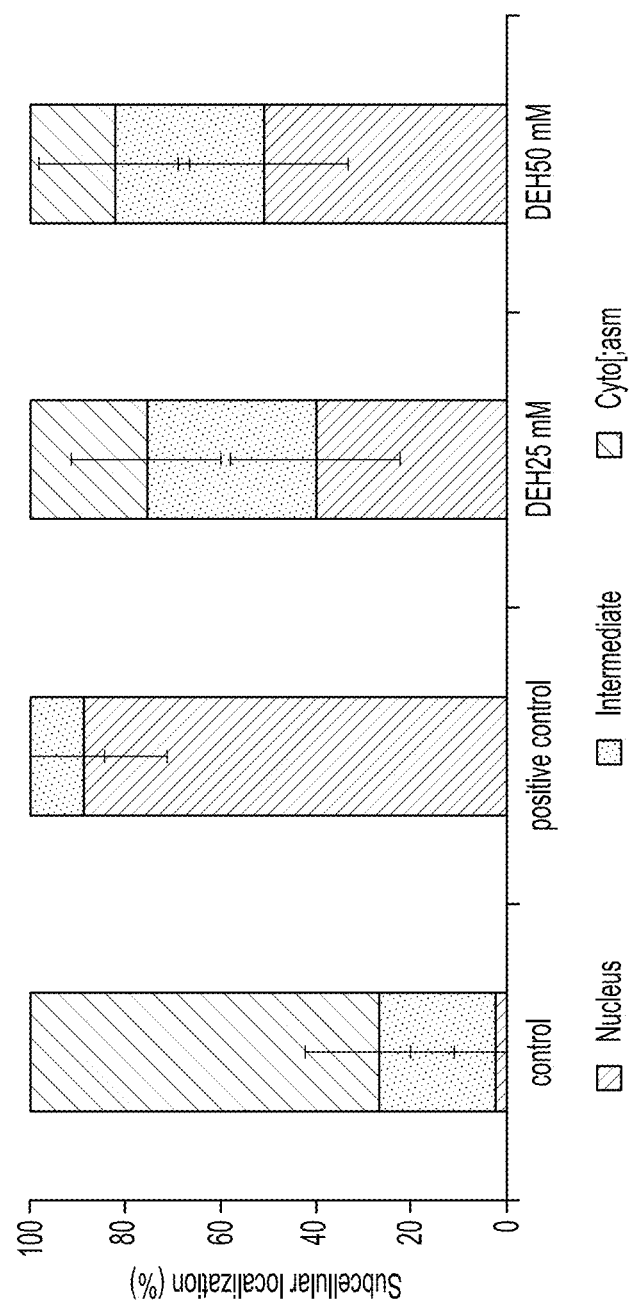
FIG. 10 is a graph showing the results in which the involvement of DEH in the expression and activation of DAF-16 was analyzed.

FIG. 10 shows the results of an examination of the nuclear localization rate of DAF-16 of *C. elegans* TJ365 strain in medium containing each sample. Each data is shown as mean±standard error. The nuclear localization rate of the Control was 2.2%, while that of the 25 mM DEH-treated group was 40.0%, and that of the 50 mM DEH-treated group was 51.1%. In addition, the intermediate localization rate of the Control was 24.4%, while that of the 25 mM DEH-treated group was 35.6%, and that of the 50 mM DEH-treated group was 31.1%. Thus, DEH increased the nuclear localization ratio of DAF-16 as compared to the Control. DEH was found to activate genes involved in stress response and longevity by promoting the localization of DAF-16 in the nucleus.

Thus, according to this embodiment, DEH could be provided as a preventive and/or therapeutic composition for neurodegenerative diseases.

The invention claimed is:

1. A method of treating a neurodegenerative disease in a patient in need thereof comprising administering a therapeutically effective amount of 4-deoxy-L-erythro-5-hexoseulose uronic acid (DEH) as a nerve growth factor (NGF) activity promoter.

2. The method of claim 1, wherein the neurodegenerative disease is at least one selected from the group consisting of PolyQ disease, Parkinson's disease, Parkinson's syndrome, spinocerebellar degeneration, spastic paraplegia, amyotrophic lateral sclerosis, Alzheimer's disease, dementia with Lewy bodies and corticobasal degeneration.

3. The method of claim 1, wherein the neurodegenerative disease is dementia.

4. The method of claim 3, wherein 4-deoxy-L-erythro-5-hexoseulose uronic acid (DEH) is administered via the intestinal tract.

5. The method of claim 4, wherein a therapeutically effective amount of nerve growth factor (NGF) is co-administered with 4-deoxy-L-erythro-5-hexoseulose uronic acid (DEH).

6. The method of claim 1, wherein 4-deoxy-L-erythro-5-hexoseulose uronic acid (DEH) is administered via the intestinal tract.

7. The method of claim 1, wherein a therapeutically effective amount of nerve growth factor (NGF) is co-administered with 4-deoxy-L-erythro-5-hexoseulose uronic acid (DEH).

8. A method of preventing a neurodegenerative disease in a patient in need thereof comprising administering a prophylactically effective amount of 4-deoxy-L-erythro-5-hexoseulose uronic acid (DEH) and a nerve growth factor (NGF) activity promoter.

9. The method of claim 8, wherein the neurodegenerative disease is at least one selected from the group consisting of PolyQ disease, Parkinson's disease, Parkinson's syndrome, spinocerebellar degeneration, spastic paraplegia, amyotrophic lateral sclerosis, Alzheimer's disease, dementia with Lewy bodies and corticobasal degeneration.

10. The method of claim 8, wherein the neurodegenerative disease is dementia.

11. The method of claim 10, wherein 4-deoxy-L-erythro-5-hexoseulose uronic acid (DEH) is administered via the intestinal tract.

12. The method of claim 11, wherein a prophylactically effective amount of nerve growth factor (NGF) is co-administered with 4-deoxy-L-erythro-5-hexoseulose uronic acid (DEH).

13. The method of claim 8, wherein 4-deoxy-L-erythro-5-hexoseulose uronic acid (DEH) is administered via the intestinal tract.

* * * * *